United States Patent [19]

Uusitalo et al.

[11] 4,412,451
[45] Nov. 1, 1983

[54] METHOD AND APPARATUS FOR THE DETERMINATION OF THE AVERAGE PARTICLE SIZE IN A SLURRY

[75] Inventors: Seppo J. Uusitalo; Georg C. von Alfthan, both of Espoo; Tor S. Andersson, Luoma; Väinö A. Paukku, Espoo; Lasse S. Kähärä, Espoo; Erkki S. Kiuru, Espoo, all of Finland

[73] Assignee: Outokumpu Oy, Helsinki, Finland

[21] Appl. No.: 399,002

[22] Filed: Jul. 16, 1982

Related U.S. Application Data

[63] Continuation of Ser. No. 151,778, May 21, 1980, abandoned.

[51] Int. Cl.³ .................... G01N 29/00; G01N 15/00; G01N 7/00
[52] U.S. Cl. ................................. 73/432 PS; 73/599; 73/61 R
[58] Field of Search ................ 73/61 R, 432 PS, 625, 73/599

[56] References Cited

U.S. PATENT DOCUMENTS

| | | | |
|---|---|---|---|
| 2,755,662 | 7/1956 | Swengel | 73/599 |
| 2,966,056 | 12/1960 | Heller | 73/599 |
| 3,710,615 | 1/1973 | Johnson et al. | 73/61 R |
| 3,774,717 | 11/1973 | Chodorow | 73/599 X |
| 3,779,070 | 12/1973 | Cushman et al. | 73/432 PS |
| 4,026,157 | 5/1977 | Goebbels | 73/432 PS |

FOREIGN PATENT DOCUMENTS

58215  8/1980  Finland .

*Primary Examiner*—Stephen A. Kreitman
*Assistant Examiner*—David V. Carlson
*Attorney, Agent, or Firm*—Brooks, Haidt, Haffner & Delahunty

[57] ABSTRACT

The average particle size for particles distributed in a slurry is determined by transmitting at least one beam of ultrasonic rays of a certain frequency into the slurry, detecting, by separate detector means, on one hand ultrasonic radiation that passes through the slurry and, on the other hand, ultrasonic radiation scattered in the slurry, said detector means forming first and second signals corresponding to the intensities of the passed-through and the scattered radiation respectively, determining the scattering attenuation factor on the basis of said first and second signals and the total attenuation factor by using the intensity of passed-through radiation obtained with pure water, and determining the particle size with the help of the scattering attenuation factor, whereby the radio of said factor and the total attenuation factor is formed in order to eliminate influence of the slurry density. Two transmitters operating at different frequencies may be used, whereby one detector may detect passed-through radiation at one frequency and the other detector may detect scattered radiation at the other frequency.

7 Claims, 14 Drawing Figures

METHOD AND APPARATUS FOR THE DETERMINATION OF THE AVERAGE PARTICLE SIZE IN A SLURRY

This is a continuation, of application Ser. No. 151,778, filed May 21, 1980 now abandoned.

BACKGROUND OF THE INVENTION

1. Field of the Invention

The present invention relates to a method and an apparatus for the determination of the average particle size in a slurry by using ultrasonic radiation.

2. Description of the Prior Art

Ultrasonic sound is attenuated in a slurry by losses due to viscosity and scattering. The attenuation is dependent primarily on the size of the slurry particles, their proportion of the volume, and the frequency used. The specific gravity of the particles also has some effect. In addition to attenuation the share of scattering can be measured directly by placing the receiver outside the radiation cone of the transmitter-sensor. By combining the data concerning scattering and attenuation, the effect of the density of the slurry can in theory be totally eliminated and an average particle size can be obtained which weights the various size categories approximately by their proportions of the volume. If the shape of the particle size distribution is approximately retained, the result can further be converted to the sieve residue percentage.

Attenuation of ultrasonic sound and the related scattering have been studied quite extensively even in connection with particle size measuring. Applications of direct measuring of scattering are rarely described, but the theory has been treated rather widely in the literature.

U.S. Pat. No. 3,779,070 to Cushmon et al. uses two ultrasonic sound frequencies, which are selected according to the criteria given in the specification and in such a manner that both the particle size and the solids content of the slurry can be determined. Even though, in some cases, one of the frequencies is selected so that the predominant mechanism determining the attenuation is scattering, this known method is characterized in that the only phenomenon that is detected and treated further in the method is the radiation intensity which has passed through and not the scattered ultrasonic radiation.

SUMMARY OF THE INVENTION

This invention provides a method which comprises transmitting at least one beam of ultrasonic rays, having a certain frequency, into the slurry, detecting ultrasonic radiation which has passed through the slurry, creating a first signal corresponding to the intensity Ia of the detected radiation, detecting in a selected direction ultrasonic radiation scattered in the slurry, creating a second signal corresponding to the intensity Is of the detected scattered radiation, determining the scattering attenuation factor on the basis of the first and second signals thus obtained, determining the total attenuation factor with the aid of the the intensity Io of passed-through ultrasonic radiation obtained in pure water, and determining a measure descriptive of the average particle size with the aid of the scattering attanuation factor, whereby the ratio of the scattering attenuation factor and the total attenuation factor is formed in order to eliminate the influence of slurry density.

Accordingly, the particle size analyzer of this invention comprises at least one ultrasonic transmitter provided to transmit a beam of ultrasonic rays at a certain frequency into the slurry to be analyzed, a first ultrasonic sensor for receiving the attenuated ultrasonic radiation which has passed through, first detector means for producing a first signal, corresponding to the intensity of the received ultrasonic radiation, a second ultrasonic sensor for receiving the scattered ultrasonic radiation, second detector means for producing a second signal, corresponding to the intensity of the scattered ultrasonic radiation, and circuit members for comparing the first and the second signal with each other and for forming a quantity describing the particle size on the basis on the result of the comparison.

Thus an essential observation according to this invention is that the average particle size can be determined with greater precision than previously, and independently of the rather wide variation of the solids content of the slurry, by measuring and using even that radiation which has scattered in a selected direction.

Before describing the method according to the invention and the analyzer for carrying out the method in more detail, it is appropriate to discuss in greater detail the theory underlying the invention, i.e. the absorption and scattering of ultrasonic sound in a slurry.

The scattering and attenuation of plane waves. The amplitude of ultrasonic sound is attenuated in a slurry according to the formula $$A_a = A_0 e^{-\alpha x} \quad (1)$$

where x is the distance traveled by the sound in the slurry $A_o$ is the amplitude of the ultrasonic wave received when there is no absorption (i.e. when the sample is pure water), and $A_a$ is the amplitude of the ultrasonic wave received when the sample contains particles which cause absorption. At moderate densities of the slurry the attenuation coefficient $\alpha$ is $$\alpha = P\mu_a, \quad (2)$$

where
P = solids content of the slurry (proportion of volume)
$\mu_a$ = specific attenuation.

The intensity is respectively $$I_a = I_0 e^{-2\alpha x} \quad (3)$$

Where
$I_o$ is the intensity of ultrasonic radiation when there is no absorption, proportional to $A_o^2$; and
$I_a$ is the intensity of ultrasonic radiation when there is absorption, proportional to $A_a^2$.

On the other hand, the attenuation coefficient can be written $$\alpha = \alpha_v + 1/(\alpha_s^{-1} + \alpha_d^{-1}), \quad (4)$$

$$\text{where } \alpha_v = p \frac{18\gamma^2(1 + \gamma)(SG - 1)^2 w/v}{81(1 + \gamma)^2 + \gamma^2[9 + 4\gamma(SG + \frac{1}{2})]^2} \; 8.68 \text{ dB/cm} \quad (5)$$

$$= \text{viscosity loss term}$$

$$\alpha_S = \frac{P}{6} \left(\frac{w}{v}\right)^4 a^3 \left[ gK^2 + \right. \quad (6)$$

-continued $$3g_s^2\left(1 - \frac{6SG}{\gamma(2SG + 1)}\right) \quad 8.68 \text{ dB/cm}$$

= scattering loss term $$\alpha_d = P(w/v)^{\frac{1}{2}}/4\pi a \quad 8.68 \text{ dB/cm} \quad (7)$$

Figure 1:
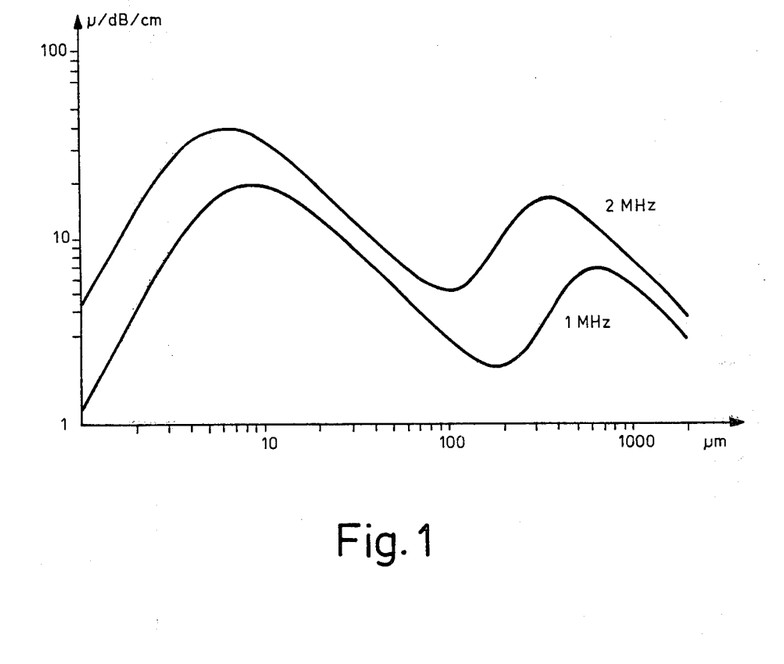
FIG. 1 depicts specific attenuation as a function of the particle size.

= diffraction loss term $w = 2\pi f$ $\gamma = a\sqrt{w/2v}$ $f$ = frequency/Hz $v$ = kinematic viscosity of water/cm²/s $v$ = velocity of sound/cm/s $SG$ = specific gravity of particles = $\rho_p$ $a$ = radius of particles/cm $g_K = \dfrac{K - K_O}{K_O}$ $K_1, K_O$ = compressibilities of particles and of water $g_s = \dfrac{SG - 1}{2SG + 1}$ Attenuation as a function of the particle size is illustrated by a two-peak curve such as shown in FIG. 1.

The decrease in the intensity of a ray, due to scattering, per a unit of travel, is proportional to the scattering loss term $\alpha_s$ and to the intensity of the ray. The scattered intensity is distributed unevenly at different angles of scattering. It can be written $$I_s = 2k\alpha_s I_0 e^{-2\alpha x} \quad (8)$$

where k is a factor dependent on the geometry and x is the total distance traveled by the sound before and after scattering. The expression sould be integrated over the scattering volume, since scattering from different points has distances of different length. At this stage, however, the scattering has been assumed to take place from the center of the measuring chamber, where the cones of the transmitter and the receiver intersect.

The radiation $I_s$ which has passed through and the scattered radiation have, in the testing system used in this case, traveled over equal distances. Their intensity ratio is $$I_s/I_a = 2k\alpha_s \quad (9)$$

On the other hand $$\alpha = \frac{1}{2x} \ln \frac{I_O}{I_a} \quad (10)$$

where $I_O$ is the intensity obtained with only water. By dividing these on each side the test quantity $$Z = k' \frac{\alpha_s}{\alpha} - \frac{I_s}{I_a \ln(I_O/I_a)} \quad (11)$$

is obtained, which is no longer dependent on the density of the slurry but only on the particle size at a certain frequency, geometry, etc.

Figure 2:
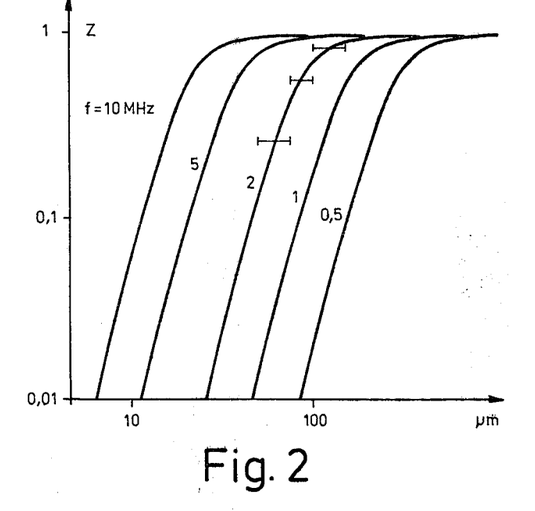
FIG. 2 depicts the dependence of the test quantity on the diameter of the particles.

The particle size dependence of the characterizing quantity Z is in accordance with FIG. 2. The dependence is very strong at a sufficiently low frequency. On the other hand, the frequency must not be unnecessarily low because then the scattering intensity decreases too much and the measurement will be imprecise. Scattering and absorption can also be measured at different frequencies.

Effect of Particle Size Distribution

Particles in a slurry have a certain size distribution. When calculating attenuation, etc., the respective quantities for the various particle sizes, weighted by the particle size distribution, must be added together. Often the log-normal distribution is used, its density function being $$f(M) = \frac{1}{\sqrt{2\pi} \ln\sigma} \exp - \left[\frac{\ln((M - M_O)(M_\infty - M_O)/(M_\infty - M)\overline{M})}{\sqrt{2} \ln\sigma}\right]^2 \quad (12)$$

where $\sigma$ = standard deviation of the geometry
M = diameter of particles = $2a$
$M_O$ = minimum particle size
$M_\infty$ = maximum particle size
$\overline{M}$ = geometric mean of particle size.

Thus the specific attenuation for a particle size distribution $$\alpha = \int_{M_O}^{M_\infty} f(M)\alpha_a d\ln \frac{M - M_O}{M_\infty - M}, \quad (13)$$

and the scattering is obtained by a corresponding method. The general characteristics of the attenuation curve are retained, but the curve becomes less sharp and the position of the minimum shifts to some extent. The particle size distribution (12) is in fairly good agreement with measured sieve analyses when suitable parameters are used.

Figure 3:
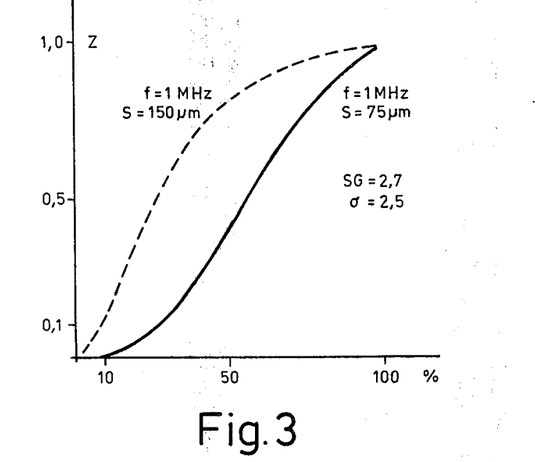
FIG. 3 depicts a comparison of the test quantity and the sieve residue percentage using two different seives, $S=75$ μm and $S=150$ μm.

The characterizing quantity (11) as a function of the sieve residue percentage is rather linear within a wide variation range, as seen in FIG. 3. It is not very sensitive even to the shape of the distribution; a two-peak distribution, $\overline{M}$ = 50 μm and 100 μm, caused an error of less than 2%.

Precision Estimate

The effect of the variation of the different factors on the results yielded by the apparatus which have been studied theoretically, and the optimum frequencies, at which the errors will be smallest, have been determined for the one- and two-frequency cases. The results are shown in the following table.

| Quantity | Basic value | Variation | Relative error of sieve analysis % | |
|---|---|---|---|---|
| | | | 1-frequency | 2-frequency |
| $\rho_p$ | 4.6 | 0.2 | 1.4 | 1.4 |

| Quantity | Basic value | Variation | Relative error of sieve analysis % | |
|---|---|---|---|---|
| | | | 1-frequency | 2-frequency |
| T | 15° C. | 3° C. | 1.2 | 1.2 |
| f | 2.4 MHz | 5% | 2.3 | |
| $f_1$ | 1.2 MHz | 5% | | 6.0 |
| $f_2$ | 1.8 MHz | 5% | | 10 |
| $A_{a1}$ ($A_a$) | | 1% | 4.6 | 0.2 |
| $A_{O1}$ ($A_O$) | | 1% | 0.7 | 0.2 |
| $A_{a2}$ | | 1% | | 1.5 |
| $A_{s2}$ ($A_s$) | | 1% | 4.0 | 1.7 |
| $\sigma$ | 2.5 | 0.5 | 2.4 | 3.2 |

The specific gravity $\rho$ and temperature T of the particles have the same effect in different cases. The two-frequency method seems to be more sensitive to frequency, but frequency is a precisely reproducible quantity; 5% represents the variation of the resonance frequencies of various crystals at the same nominal frequency. When the crystal is replaced, re-calibration is obviously necessary.

The two-frequency method seems to be less sensitive to errors in amplitude measurements. The range of the amplitudes measured being approximately 10-fold (factor 100 in intensity), the amplitude measurement error will obviously be a factor which limits precision; this would favour the use of the frequencies. There is not a very great difference regarding the standard deviation of the distribution. Owing to its variations, approximately 3% is the limit for the precision which can be attained in the residue percentage.

The plane wave observation corresponds to a case in which the transmitter and the receiver are far from the scattering area (compared with a sensor size of 15 mm and a wavelength of approximately 1 mm) and the scattering area is small. This is not true in practice, but the difference has been included in the geometric factor k' in the formula (11). The factor has been determined from test results. In this case, curves highly congruent with the test results were obtained as a function of the particle size, and in practice this is the most immportant condition. The congruence is, however, less when the curves are obtained as a function of frequency. This is natural since the geometric factor is dependent on the wavelength, and thus on the frequency.

Scattering occurs from the entire area of the measuring chamber. The area is delimited by using transmitter pulses and receiver gating of finite length. Furthermore, the widths of the radiation cones of the transmitter and the receiver delimit the area. Finally, the time discrimination is taken into account; it excludes scattering which has occurred too far from the assumed area.

The theory described above has thus been applied in the present invention. When measurements were performed, the quantities characterizing scattering and absorption as functions of the particle size did behave in accordance with the theory. Reaching compatibility as a function of the frequency required the taking into account of the finite geometry of the measuring space and the time length of the transmitter pulses and the receiver gating. A small addition was made to the expressions; this addition takes into account the effect that the specific gravity and compressibility of the particles have on the scattering. Thereafter the agreement between the theory and the tests was high with all successful measurements. However, the number of reliable test results so far obtained is relatively low.

DESCRIPTION OF THE PREFERRED EMBODIMENTS

Of the figures listed above, FIGS. 1-3 have already been described. FIGS. 2 and 3 show the theoretical curves when only a single frequency is used, whereas figures 12 to 14 pertain to cases when two different frequencies are used, including the experimental points as well as corresponding theoretical curves (solid lines).

Figure 4:
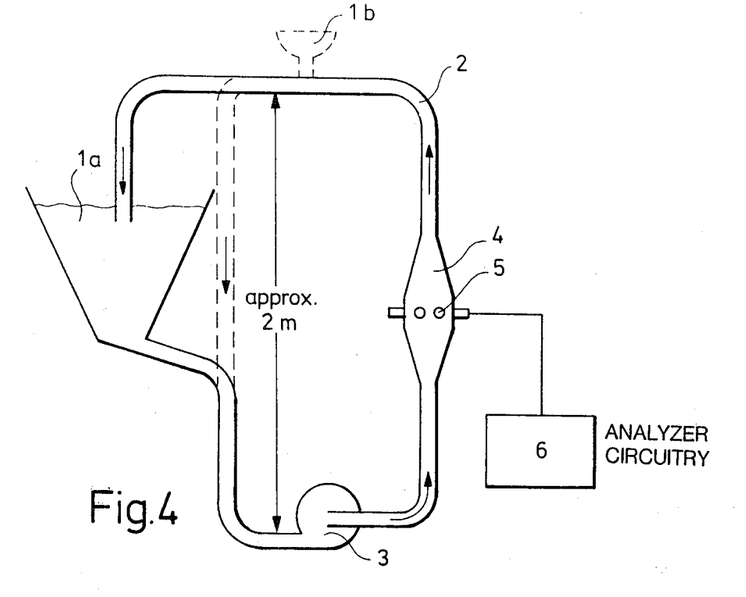
FIG. 4 depicts diagrammatically one experimental apparatus intended for applying the invention.

FIG. 4 depicts the experimental apparatus intended for carrying out the invention. Reference numerals 1a and 1b indicate alternative filling tanks from which the slurry to be studied is fed into the pipe loop 2. The slurry is circulated by means of a pump 3, and a measuring cell 4 and sensors 5 have been positioned in the vertical part of the loop. The sensors 5 have also been connected to the electronics part 6 of the analyzer, described in greater detail below.

Figure 5:
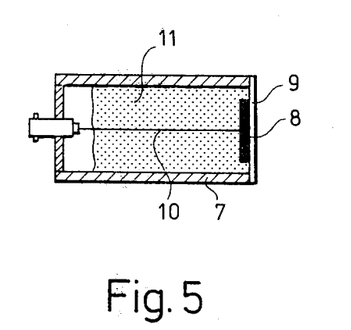
FIG. 5 depicts the structure of an ultrasonic sensor.
Figure 6:
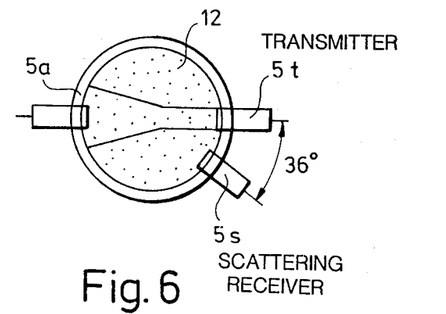
FIG. 6 depicts one geometry of the measuring cell.

FIG. 5 depicts one ultrasonic sensor which has been designed specifically for this analyzer. Numeral 7 indicates the metal frame of the sensor, 8 the ultrasonic crystal, and 9 the titanium plate glued to the end of the sensor to protect the crystal. A connecting wire 10 extends through the sensor, and the inside of the frame has been filled with araldite resin 11. The sensors can be placed in the measuring cell in, for example, the manner shown in FIG. 6. In the figure, the sensor part serving as a transmitter is indicated by $5_t$, the sensor measuring the ultrasonic radiation which has passed through and part of which has thus been absorbed in the slurry is indicated by $5_a$, and the sensor measuring scattered radiation is indicated by $5_s$. In order to eliminate disturbing echoes, the inside of the cell has been lined with rubber 12.

Figure 7:
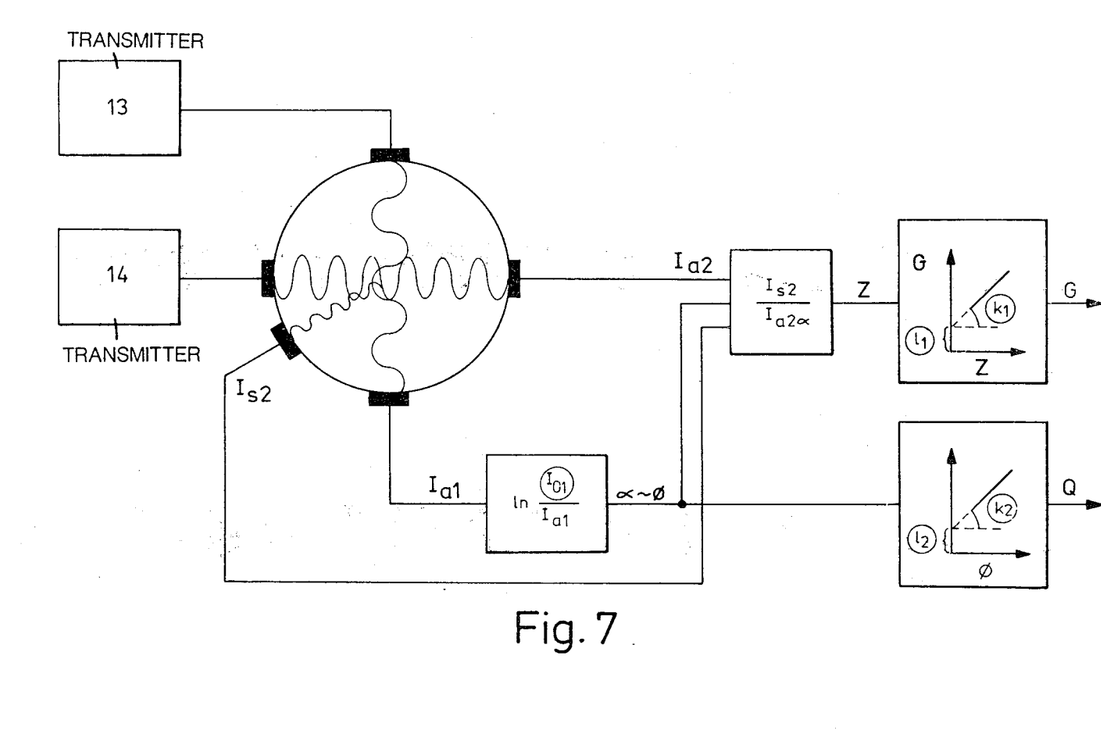
FIG. 7 depicts diagrammatically the layout of the ultrasonic particle size analyzer according to the invention.

FIG. 7 depicts a layout drawing of the ultrasonic particle size analyzer. In the analyzer, elements 13 and 14 are transmitters and in addition the cell has two receiving absorption sensors and one sensor for scattering. I indicates intensities, k and l are the constants determining the calibration straight lines, $\rho$ is the density of the slurry, $\phi$ is the volume proportion of the particles, and G is the quantity representing the sieve analysis. The encircled quantities must be determined by calibration measurements, i.e. by using fractions of known particle size, suspended in the slurry.

Figure 8:
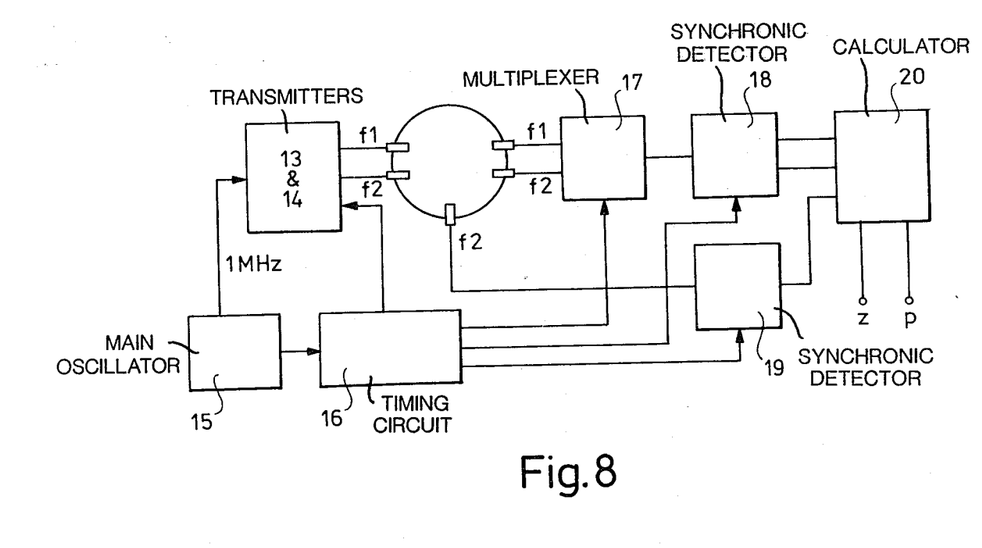
FIG. 8 depicts a block diagram of the particle size analyzer.

A block diagram corresponding to FIG. 7 is depicted in FIG. 8. Numeral 15 indicates the main oscillator which feeds a signal at a frequency of 1 MHz to both of the transmitters 13 and 14 and to the timing circuit 16, which serves to synchronize the transmitting side and the receiving side. Numeral 17 indicates the multiplex device, which receives signal frequencies $f_1$ and $f_2$ and from which these are further carried to the synchronic detector 18. The signal from the sensor receiving the scattered ultrasonic sound is carried to the synchronic detector 19. The signals are further carried from the detectors 18 and 19 to the calculating unit 20.

The transmitters send, alternately to each sensor, pulses with a length of approx. 20 μs and a frequency of 0.5–4 MHz, the reproduction frequency of the pulses being approximately 1 kHz. In the receiver part these high-frequency pulses are detected synchronically, and data proportional to the residue percentage and the density of the slurry are formed from the voltages corresponding to their amplitudes in the calculating unit.

Figure 9:
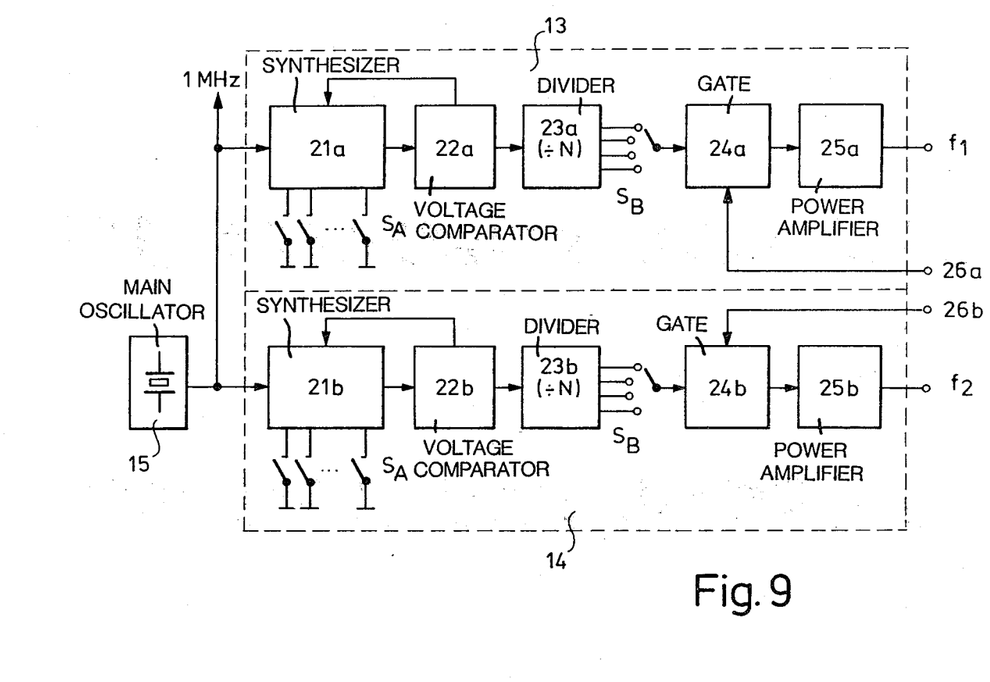
FIG. 9 depicts a block diagram of the transmitter of the analyzer.

The details of the transmitter part are shown in FIG. 9. In order to ensure a sufficient stability of frequency, the transmitters have been synchronized with a main oscillator of 1 MHz. All the necessary frequencies can be produced from this fundamental frequency by means of the synthesizer pair 21a, 21b. Four frequency ranges can be selected by means of switches $S_B$: 250–500 kHz, 500–1000 kHz, 1–2 MHz, and 2–4 MHz. Fine adjustment within each range can be performed by means of the switch series $S_A$. The extent of the smallest frequency step varies according to the frequency range, being 3.125 kHz within the lowest and 25 kHz within the highest range.

The signals obtained from the synthesizers 21a and 21b are compared in a phase-locked loop to VCU voltages (blocks 22a and 22b), the frequency and the phase diffrence are corrected, and the signal frequency is divided by N in circuits 23a and 23b. The signals thus obtained are connected via gates 24a and 24b to the power amplifiers 25a and 25b, which control the ultrasonic sensors. The gates are controlled by means of the timing circuit 16 via connections 26a and 26b.

The end stages are capable of feeding a voltage of approximately 40 $V_{pp}$ to the load, which has proved sufficient in practice. Owing to the structure of the sensors, their impedances are highly reactive even at their resonance frequency. For this reason, when feeding-cable lengths longer than 1 m are used, end resistors of 50 Ω must be installed inside the transmitter sensors in order that the produced standing waves will not damage the end stages.

The stabilization of the amplitude is easy to provide for when the amplifier is designed as a so-called switch amplifier. In this case, depending on the input signal, either a positive or a negative feed voltage is connected to the load, and thereby the stabilization of the amplitude can be performed as direct-voltage control.

When the control signal of the transmitters consists of squate waves, it also contains the odd harmonics of the fundamental frequency. It has been verified by experiments that in pure water, depending on the sensor type, the transmission of the third harmonic is at its worst approximately 10% of the transmission of the fundamental wave. However, the amplitude of the 3rd harmonic is only 33% of the fundamental wave, and so at maximum approximately 3% of the received signal consists of the third harmonic. In slurry measuring, this value further decreases significantly.

Figure 10:
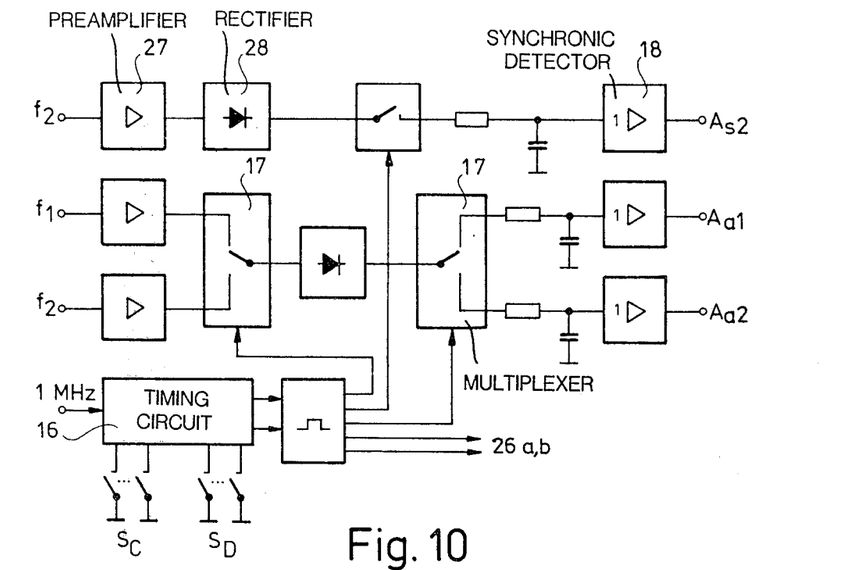
FIGS. 10 and 11 depict block diagrams of the calculating unit of the analyzer.

The receiver part is as shown in FIG. 10. Since the ultrasonic signals received, especially scattering, are of random nature, special attention has been paid to detection. In connection with the tests performed, it was observed that the fact whether the intensities of the signals are measured as effective values or as arithmetic time mean values does not have a noteworthy effect on the results of measurement. It has possible to simplify the structure of the receiver on the basis of this observation. The preamplifier 27, the rectifier 28, and the synchronic detector 18 constitute one receiver channel, the entire receiver containing three of them: two for measuring scattering and absorption at the frequency $f_2$ and one for measuring absorption at the frequency $f_1$. Since the frequencies $f_1$ and $f_2$ are transmitted as pulses at different times, the absorption signals $A_{a1}$ and $A_{a2}$ can be measured with one and the same rectifier 28 by multiplexing the signals by means of the multiplex device 17.

The timing circuit 16 also receives its control from the 1 MHz main oscillator. The reproduction frequency of pulses is adjusted to a suitable value by means of the switch series $S_C$ and $S_D$ and the timely placing of the measuring gating is adjusted so that it is correct for the synchronic detectors 18. It has been observed that the interval between successive transmitter pulses must be at minimum 500 μs in order that the scattered echoes caused by the first could die down before the measuring of the next one. The length selected for the transmitter pulse is 20 μs. A shorter pulse cannot be used since the filtering of the receiver would integrate the pulse height too much. A longer transmitter pulse is out of the question since, for its part, it would cause interferences in the receiver because of the rather short (approx. 60 μs) travel time of the signal.

Figure 11:
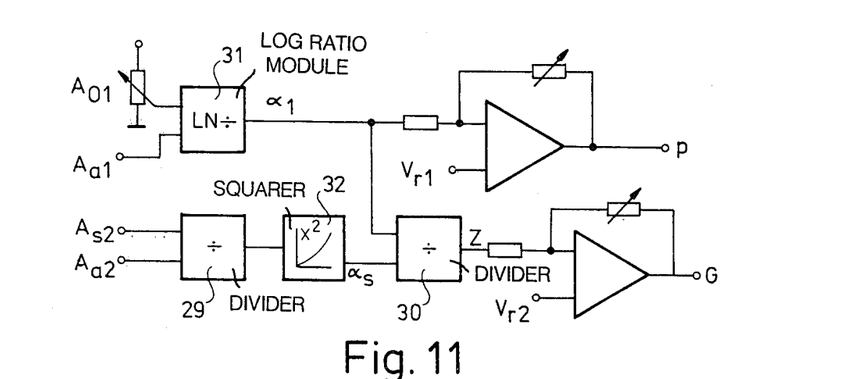

The characterizing quantity Z and the density of the slurry S can be produced by means of the calculating unit illustrated in FIG. 11. It has two dividers 29 and 30 and one log-ratio module 31 and a squarer 32. During calibration using water, the $A_{O1}$ potentiometer is adjusted. The frequencies have been selected so that α is a quantity approximately proportional to the density of the slurry. The residue percentage is obtained from the characterizing quantity Z by approximating it with a straight line having adjustable angle coefficient and an adjustable place of the origin. The output of the density of the slurry is scaled by the same procedure.

The factor which has the strongest effect on the precision of the calculating unit is the density of the slurry. According to the specifications, under operating conditions the density of slurry varies at its worst at a ratio of 1:3.

In practice, a precision of 0.1% of the full initial value is obtained with the divider modules, and a precision of 0.5%, reduced to the output signal, is obtained with the log-ratio module. The effect of the density of slurry due to these errors is observed below:

| Particle size 40 μm | | |
|---|---|---|
| $A_{a1}/A_{O1}$ | max. value is approx. | 0.75 |
| $A_{s2}/A_{a2}$ | variation range is approx. | 2 |
| $α_s$ | has a max. error of | 0.4% |
| $α$ | has a max. error of | 0.9% |
| | total error | 1.3% |

| Particle size 100 μm | | |
| --- | --- | --- |
| $A_{a1}/A_{O1}$ | max. value is approx. | 0.6 |
| $A_{s2}/A_{a2}$ | variation range is approx. | 2 |
| $\alpha_s$ | has a max. error of | 0.4% |
| $\alpha$ | has a max. error of | 0.5% |
| | total error | 0.9% |

It can be observed that the calculating unit meets the given requirement of 2%.

EXAMPLES OF MEASURING

Measurements of absorption and scattering of ultrasonic sound in connection with the development of an ultrasonic particle size analyzer were performed both with water and with slurries by using the slurry circulation system described above. Since a proper air remover was not yet in use, air was allowed to escape by itself through an open vessel. Such air removal requires approximately half an hour.

Figure 12:
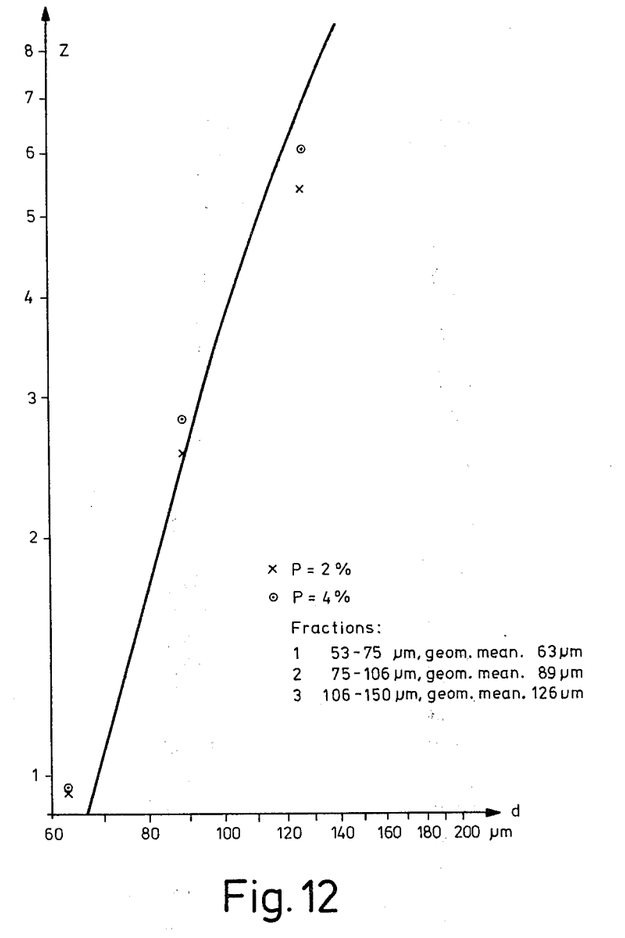
FIGS. 12-14 depict the measured values obtained with the analyzer according to the invention and the curves drawn on the basis of the same.
Figure 13:
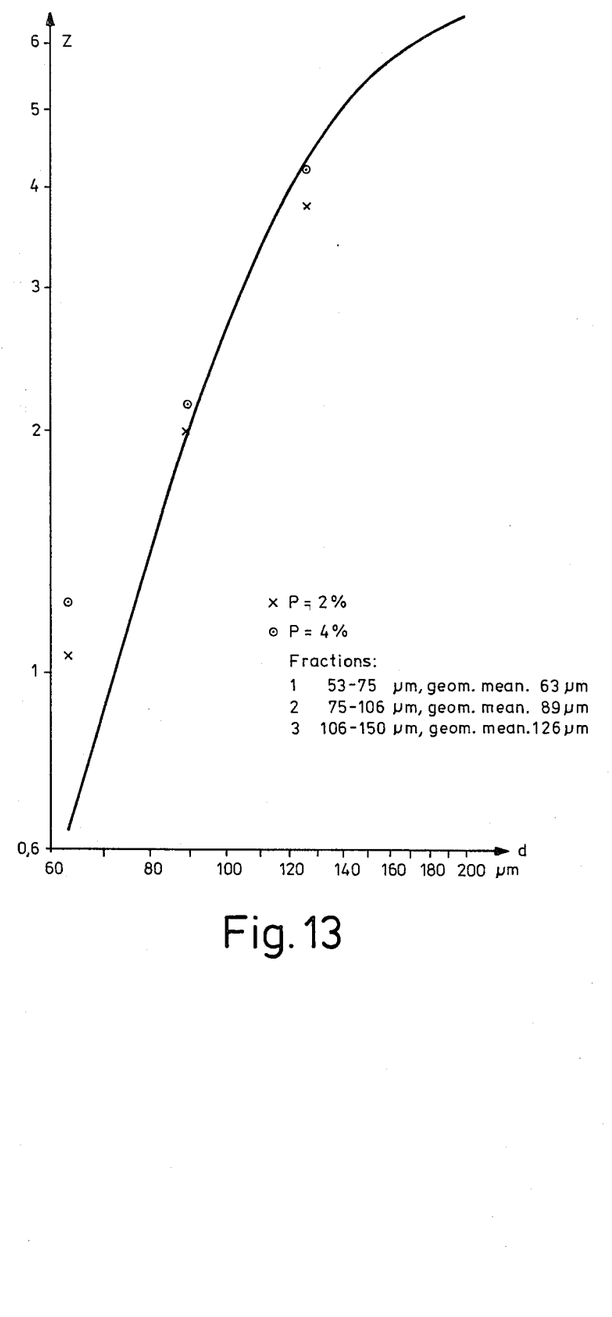

The sensors used were as shown in FIG. 5, with a titanium plate glued to protect the crystal. Sensors operating at different frequencies were used since the two-frequency method considerably improves the differentiating capacity of the specific quantity (Z) characterizing the particle size. FIGS. 12 and 13 show the values calculated for the specific quantity (Z) on the basis of measurements.

The results according to FIG. 12 were obtained by using frequencies of $f_1 = 0.95$ MHz and $f_2 = 1.9$ MHz; the frequencies of FIG. 13 were $f_1 = 1.16$ MHz and $f_2 = 1.9$ MHz. The values of the theoretical characterizers were calculated by assuming that all the particles in the material tested were the same size. The experimental results were correlated to the theoretical ones by setting the value of the characterizing quantity yielded by the experiments and corresponding to the volume proportion of the 2-percent slurry density of the middle fraction so as to equal to the characterizer of the theoretical single particle size at the particle size 89 μm.

Figure 14:
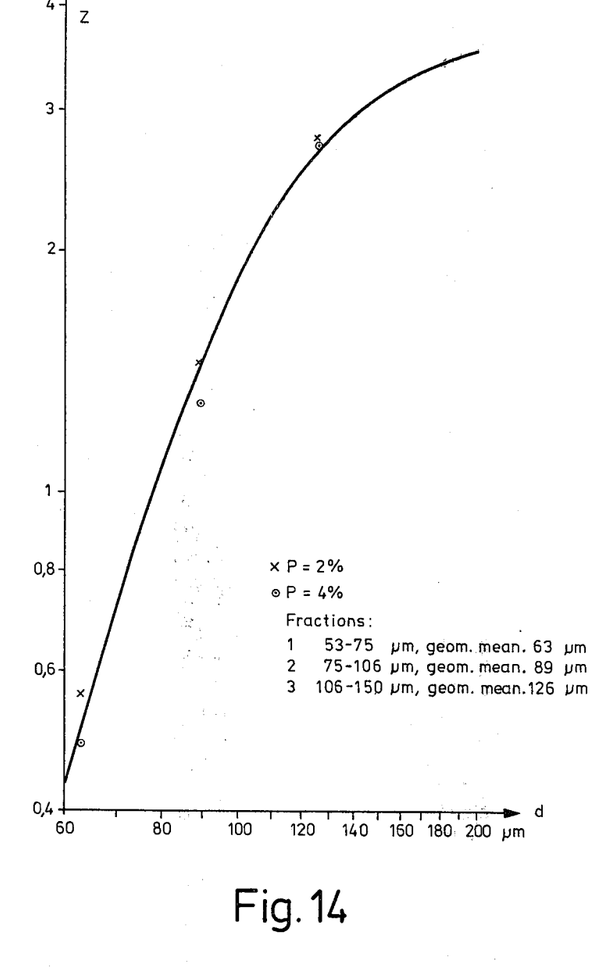

When performing the measurements of FIGS. 12 and 13, the electronics part of the analyzer was still incomplete, especially regarding the measuring of scattering. FIG. 14 illustrates a measurement which was obtained by using improved electronics and new sensors. These sensors had a stainless-steel plate protecting the crystal; the steel plate had been soldered to the crystal by using a special solder. The frequencies used were $f_1 = 1.3375$ MHz and $f_2 = 1.8625$ MHz. The correlating of the experimental to the theoretical values was as in FIGS. 12 and 13.

What is claimed is:

1. A method for the determination of the average particle size in a slurry, which comprises
    transmitting at least one beam of ultrasonic rays, having a certain frequency, into the slurry,
    detecting ultrasonic radiation which has passed through the slurry,
    creating a first signal corresponding to the intensity Ia of the detected radiation,
    detecting in a selected direction ultrasonic radiation scattered in the slurry,
    creating a second signal corresponding to the intensity Is of the detected scattered radiation,
    determining the scattering attenuation factor on the basis of the first and second signals thus obtained,
    determining the total attenuation factor with the aid of the intensity Io of passed-through ultrasonic radiation obtained in pure water, and
    determining a measure descriptive of the average particle size with the aid of the scattering attenuation factor, whereby the ratio of the scattering attenuation factor and the total attenuation factor is formed in order to eliminate the influence of slurry density.

2. A method according to claim 1, wherein two transmitter-sensors, operating at different frequencies, are used, and the attenuated radiation which has passed through is measured using the first frequency and at least the scattered radiation is measured using the second frequency.

3. A method according to claim 2, wherein both the attenuated radiation which has passed through and the scattered radiation are measured using the second frequency.

4. A particle size analyzer for determining of the average particle size in a slurry, said analyzer comprising:
    at least one ultrasonic transmitter provided to transmit a beam of ultrasonic rays, in the form of a radiation cone, at a certain frequency into the slurry to be analyzed,
    a first ultrasonic sensor for receiving the attenuated ultrasonic radiation which has passed through the slurry,
    first detector means connected to said first ultrasonic sensor for producing a first signal, corresponding to the intensity of the received ultrasonic radiation,
    a second ultrasonic sensor, situated outside the radiation cone of said beam, for receiving the scattered ultrasonic radiation,
    second detector means connected to said second ultrasonic sensor for producing a second signal, corresponding to the intensity of the scattered ultrasonic radiation, and
    circuit members for comparing the first and the second signal with each other and for forming a quantity describing the particle size on the basis of the result of the comparison.

5. An analyzer according to claim 4, comprising two transmitters operating at different frequencies for transmitting ultrasonic radiation alternatively into the slurry,
    said transmitters and detector means all being connected through a timing circuit to a mutual main oscillator, this oscillator synchronizing the transmitters and detectors respectively.

6. An apparatus according to claim 5, wherein there are two of said first ultrasonic sensors for receiving the attenuated radiation which has passed through, one of said first sensors operating at each of said two different frequencies, both of said first ultrasonic sensors being connected to said first detector means via a multiplex device.

7. An analyzer according to any one of claims 4-6, wherein an electronic calculating unit is coupled next in line to the detector means.

* * * * *